United States Patent [19]

Guala et al.

[11] Patent Number: 5,500,003
[45] Date of Patent: Mar. 19, 1996

[54] TRANSDUCER-PROTECTOR DEVICE FOR BIOMEDICAL HAEMODIALYSIS LINES

[75] Inventors: Ernesto Guala; Gianni Guala, both of Turin, Italy

[73] Assignee: Industrie Borla, S.p.A., Moncalieri, Italy

[21] Appl. No.: 338,093

[22] Filed: Nov. 9, 1994

[30] Foreign Application Priority Data

Nov. 9, 1993 [IT] Italy ................... TO93A0844

[51] Int. Cl.⁶ ....................................... A61M 1/00
[52] U.S. Cl. ............................. 604/252; 604/126
[58] Field of Search ................... 604/29, 126, 190, 604/283, 252

[56] References Cited

U.S. PATENT DOCUMENTS

| | | | |
|---|---|---|---|
| 3,520,416 | 7/1970 | Keedwell | 604/126 |
| 4,113,627 | 9/1978 | Leason | 604/126 |
| 4,459,139 | 7/1984 | vonReis et al. | 604/126 |
| 4,664,800 | 5/1987 | Raines et al. | 604/126 |
| 4,737,148 | 4/1988 | Blake | 604/126 |
| 4,828,587 | 5/1989 | Baurmeister et al. | 604/126 |
| 5,045,096 | 9/1991 | Quang et al. | 604/126 |
| 5,183,472 | 2/1993 | Jaehrling et al. | 604/252 |

FOREIGN PATENT DOCUMENTS 1096431  6/1955  France ................... 604/252

*Primary Examiner*—C. Fred Rosenbaum
*Assistant Examiner*—Manuel Mendez
*Attorney, Agent, or Firm*—Sughrue, Mion, Zinn, Macpeak & Seas

[57] ABSTRACT

Transducer-protector device for biomedical haemodialysis lines includes a body of moulded plastic material having a first tubular connector of the female Luer Lock type with a conical inner surface and an outer threading and a second tubular connector. The connectors are provided with respective first and second radial flanges for their mutual permanent sealed connection and between which a filtering membrane of permeable material is interposed. The female Luer Lock connector with the respective outer threading is entirely formed of a material having higher elasticity than the material of the second tubular connector and is fixedly coupled to the respective radial flange by overmoulding.

3 Claims, 1 Drawing Sheet

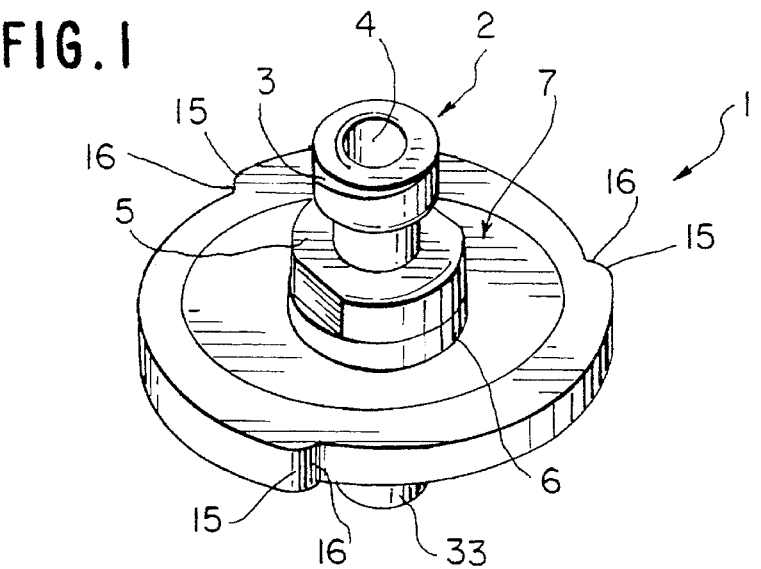
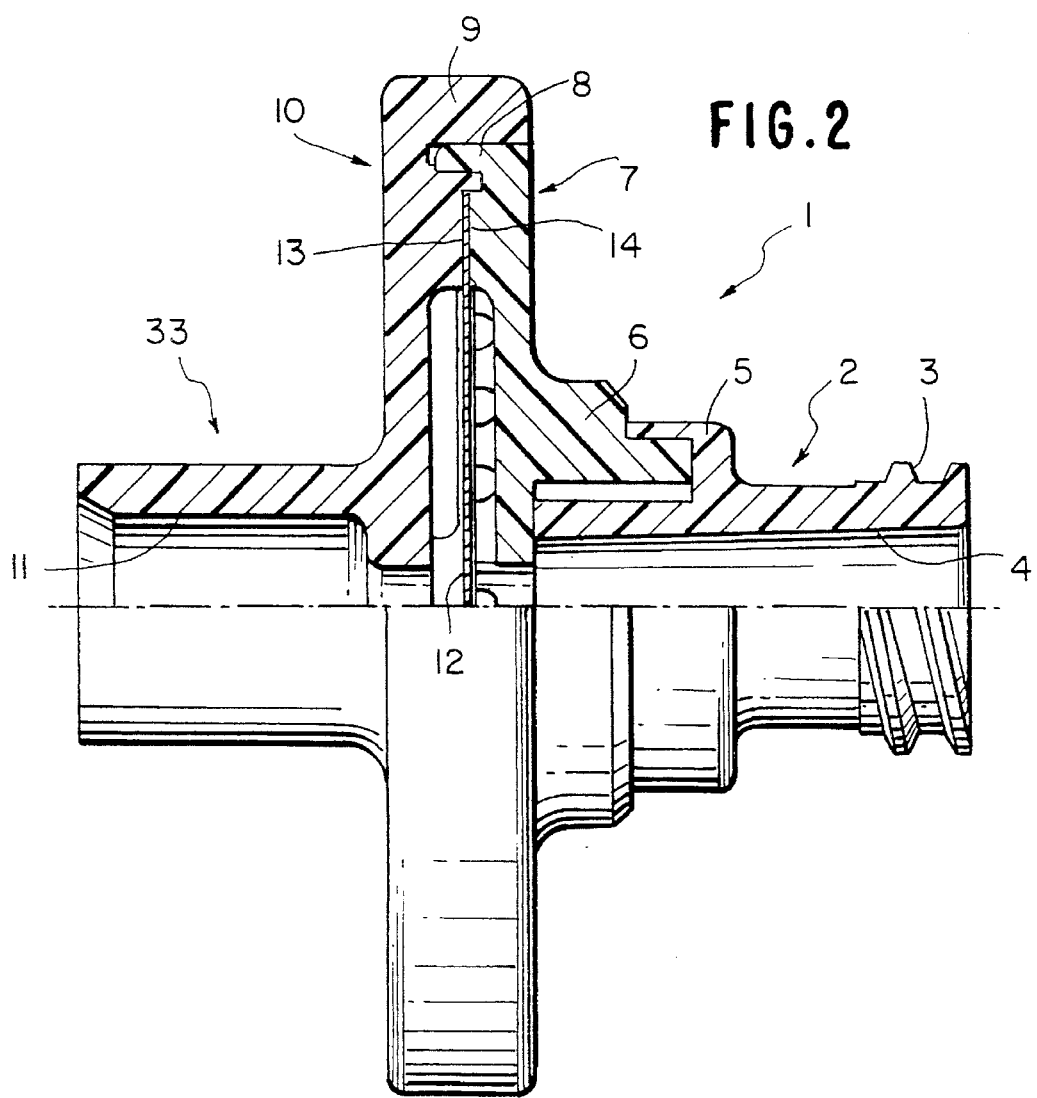

TRANSDUCER-PROTECTOR DEVICE FOR BIOMEDICAL HAEMODIALYSIS LINES

BACKGROUND OF THE INVENTION

The present invention is related to transducer-protector devices for biomedical haemodialysis Fines, of the type comprising a body of moulded plastic material having a first tubular connector of the Luer Lock female type with a conical inner surface and an outer threading, intended to be connected to a tube of a haemodialysis equipment, a second tubular connector coaxial to the first tubular connector; said first and second tubular connectors being provided with respective first and second annular radial flanges for their mutual permanent sealed connection, and a filtering membrane made of a permeable material and defining an anti-contamination sterile barrier transversally interposed between said first and second tubular connectors and having a peripheral edge clamped between said radial flanges.

Transducer-protector devices of the above-referenced type constitute essential elements in biomedical haemodialysis lines which put the dialysis equipment in connection with the patient. The primary function of the transducer element in the dialysis equipment is to continously monitor the patient's blood pressure. The protection function consists of providing a sterile barrier protecting the operators, the dialysis equipment and the patient from risks of contamination by virus-infected blood, both in liquid state and in aerosolized state, as well as to filter out any particles which might be contained in an air stream possibly fed back to the equipment for its blast cleaning.

Traditionally the body of the transducer device is made of a high resistance and high rigidity plastic material, normally polycarbonate, so as to stand sterilization operations (normally vapour and/or gamma rays sterilization or the like) before the device is put on the market. Since normally the connection between the first tubular connector and the haemodialysis equipment tube is performed through a male Luer connector made of metal (normally stainless steel) of that tube, there is the risk of a non perfectly hermetic connection, actually deriving from the high stiffness of the material of which the first tubular connector is traditionally made. As a matter of fact, even the smallest imperfection in the female and male Luer Lock coupling may result in a leakage of fluid from the connection and, therefore, in a consequent error in the measurement of the patient's blood pressure.

A solution to this problem consists of manufacturing the conical inner surface of the Luer Lock connector with a material having elasticity characteristics higher than those of the body of the device, for instance polyester or similar less rigid plastic materials, providing an insert of this material co-axially arranged within the first tubular connector and mechanically secured thereto, for instance by means of a forced fit or similar retaining systems. Such a solution has been for example proposed by the same Applicant in Italian patent application no. TO93A000368 (unpublished at the priority date of the present application).

SUMMARY OF THE INVENTION

The object of the present invention is to provide an improved solution to the above referenced problem, of a more simple and economical construction and also functionally superior.

According to the invention, this object is achieved by virtue of the fact that the entire first. Luer Lock connector along with the outer threading thereof is constituted by said material having superior elasticity characteristics, and is provided with an axially inner attachment part fixedly coupled by overmoulding onto a complementary axially outer attachment part of the respective first radial flange.

This solution can be obtained in a simple and economical way through an insert-moulding method, introducing into a mould the radial flange made for instance of polycarbonate, over which the female Luer Lock connector, for instance made of polyester, is then moulded.

Moreover the construction of the invention enables providing a female Luer Lock connector which is sufficiently flexible, and thus adapted to fit to the different male Luer connectors of the haemodialysis equipment, which may also be superficially damaged, so as to guarantee a perfect tightness under pressure and thus improving operative functionality of the device. This positive effect is further enhanced due to the fact that also the outer threading of the female Luer Lock connector is, as pointed out, made of the same more resilient material, which ensures a more effective coupling with the corresponding inner threading of the male Luer connector.

According to an other aspect of the invention, said first and second radial flanges conveniently have respective peripheral edges coupled one within the other, and the peripheral edge of said second radial flange is formed with angularly offset outer projections shaped so as to define grasping surfaces only in the :direction of rotation corresponding to unscrewing of said first Luer Lock connector.

Due to this feature easier unscrewing of the transducer-protector device relative to male Luer connectors is accomplished, owing to the fact that the handgrip defined by the outermost perimetral edge provided with said projections prevents that an excessive screwing torque be applied, ensuring on the contrary effective grasp and thus application of a high torque during unscrewing.

The two radial flanges are advantageously provided with respective annular front retaining surfaces for the peripheral edge of the filtering membrane.

The filtering membrane is thus welded between two materials which are perfectly compatible with each other, so as to obtain an optimum rigidity of the connection and enabling the membrane itself to constantly operate under the best conditions.

The invention is also directed to a method for the manufacturing of such a transducer-protector device.

BRIEF DESCRIPTION OF THE DRAWINGS

The invention will now be disclosed in detail with reference to the annexed drawings, purely provided by way of non limiting example, in which:

FIG. 1 is a diagrammatic perspective view of a transducer-protector device according to the invention, and FIG. 2 is a partially axially sectioned and enlarged view of the transducer-protector device.

DESCRIPTION OF THE PREFERRED EMBODIMENTS

Referring to the drawings, reference numeral 1 generally designates a tranducer-protector device according to the invention, for use with biomedical haemodialysis lines.

The transducer-protector device 1 comprises a first tubular connector 2, intended to be connected in use to a tube of a haemodialysis apparatus, and a second tubular connector 33 intended to be connected in use to a patient undergoing haemodialysis.

The first tubular connector is formed by a single piece of relatively elastic, flexible and soft plastic material, for instance polyester, with an outer end having external threading 3 and a conical inner surface 4 diverging towards the outer end of the connector 2. The connector 2 is thus of the female Luer Lock type, and is adapted for coupling thereof to a connector of the Luer Lock male type associated to a tube of a haemodialysis equipment.

The inner end of the connector 2 is formed with a radial-axial attachment element 5 which is permanently and rigidly secured, following an overmoulding process, to an axial attachment appendage 6 of a first annular radial flange 7 made of a moulded plastic material which is more rigid and resistant than the material of the tubular connector 2, and which is normally polycarbonate.

The annular flange 7 has a circular shape and the outer perimetral edge 8 thereof is axially bent and is engaged beneath a corresponding perimetral edge 9 of a second radial annular flange 10, which is also made of a rigid and resistant plastic material, normally polycarbonate. The peripheral edges 8 and 9 of the two flanges 7 and 10 are permanently and sealingly connected to each other, for instance by means of ultrasonic welding.

The second tubular connector 33, which is coaxial to the first tubular connector 2, is made integral with the radial flange 10 and is also provided with a conical inner surface 11 diverging outwardly.

Reference numeral 12 indicates a filtering membrane made of a permeable material and defining an anti-contamination sterile barrier radially interposed between the tubular connectors 2 and 33. The membrane 12 is clamped along its outer peripheral edge between corresponding front clamping surfaces 13 and 14 of the two radial flanges 7 and 10.

As clearly depicted in FIG. 1, the peripheral edge 9 of the annular flange 10 is outerly formed with angularly offset projections 15 defining grasp-teeth surfaces 16 only in the direction of rotation corresponding to unscrewing of the Luer Lock connector 2.

As previously pointed out, manufacturing of the transducer-protector device 1 is carried out by first moulding the radial flange 7. Subsequently the radial flange 7 is inserted within a mould for moulding thereover of the first tubular connector 2. The second tubular connector with the integral flange 10 is molded independently. Finally two flanges 7 and 10 are permanently secured to each other, following interposition of the filtering membrane 12 therebetween, by means of ultrasonic welding.

The construction employing the less stiff and more resilient material of the female Luer Lock connector 2 in its entirety, i.e. both of the inner Luer cone 4 and of the outer threading 3, enables in use the transducer-protector device according to the invention to be perfectly adaptable to any Luer Lock male connectors of haemodialysis equipment, so as to guarantee in any case a total fluid-tight connection under pressure. Moreover, as explained in the above, unscrewing of the transducer-protector device relative to the Luer Lock male connector is made more convenient by virtue of both flexibility of the outer threading 3 of the tubular connector 2, and of the shape of the peripheral grasp projections 15, which does not allow application of an excessive screwing torque and ensures on the contrary an efficient grip during unscrewing.

Naturally the details of constructions and the embodiments may be widely varied with respect to what has been disclosed and illustrated, without thereby departing from the scope of the present invention, such as defined in the appended claims.

What is claimed is:

1. A transducer-protector device for biomedical haemodialysis lines, comprising a body of moulded plastic material having a first tubular connector of the Luer Lock female type with a conical inner surface and an outer threading, intended to be connected to a tube of a haemodialysis equipment, and a second tubular connector coaxial to said first tubular connector, said first and second connectors being provided with respective first and second radial annular flanges for their mutual permanent sealed connection, and a filtering membrane made of a permeable material and defining an anti-contamination sterile barrier transversely interposed between said first and second tubular connectors and having a peripheral edge clamped between said radial flanges, wherein the entire first tubular connector is made of a material having greater elasticity than the material of the second connector, wherein said first radial flange is provided with a first integral axial attachment part, and wherein the first connector is provided with a second integral axial attachment part fixedly coupled by overmoulding onto said first axial attachment part of said first radial flange.

2. Transducer-protector device according to claim 1, wherein said first and second radial flanges have respective peripheral edges coupled one within the other, and in that the peripheral edge of said second flange is formed with angularly spaced outer projections shaped so as to define grasping surfaces only in the direction of rotation corresponding to unscrewing of said first Luer Lock connector.

3. Transducer-protector device according to claim 1, wherein said first and second radial flanges have respective annular front retaining surfaces for the peripheral edge of the filtering membrane.

* * * * *